United States Patent
Soni et al.

(10) Patent No.: US 7,785,611 B2
(45) Date of Patent: Aug. 31, 2010

(54) PARENTERAL VACCINE FORMULATIONS AND USES THEREOF

(75) Inventors: Nanna Kristensen Soni, Copenhagen K (DK); Janne Uldal Rahbek, Holte (DK); Stig Aasmul-Olsen, Skodsborg (DK); Lise Lund, Fredensborg (DK)

(73) Assignee: ALK-Abello A/S, Horsholm (DK)

( * ) Notice: Subject to any disclaimer, the term of this patent is extended or adjusted under 35 U.S.C. 154(b) by 0 days.

(21) Appl. No.: 11/150,442

(22) Filed: Jun. 9, 2005

(65) Prior Publication Data

US 2005/0244420 A1 Nov. 3, 2005

Related U.S. Application Data

(63) Continuation of application No. 09/925,635, filed on Aug. 9, 2001, now abandoned.

(60) Provisional application No. 60/224,037, filed on Aug. 9, 2000.

(30) Foreign Application Priority Data

Aug. 9, 2000 (DK) ............................ 2000 01194

(51) Int. Cl.
- *A61K 39/00* (2006.01)
- *A61K 43/00* (2006.01)
- *C12N 7/00* (2006.01)

(52) U.S. Cl. ................ 424/278.1; 424/184.1; 424/1.11; 424/93.1; 435/5

(58) Field of Classification Search ........................ None
See application file for complete search history.

(56) References Cited

U.S. PATENT DOCUMENTS

| | | | |
|---|---|---|---|
| 3,148,121 A | 9/1964 | Strauss | |
| 3,329,564 A | 7/1967 | Aguiar et al. | |
| 3,692,898 A * | 9/1972 | Gorman et al. | 424/689 |
| 4,233,288 A | 11/1980 | Cornell | |
| 4,341,763 A | 7/1982 | Zygraich et al. | |
| 4,913,909 A | 4/1990 | Hara et al. | |
| 5,032,405 A | 7/1991 | Huang et al. | |
| 5,232,690 A | 8/1993 | Bernhardt et al. | |
| 5,338,543 A | 8/1994 | Fitzgerald et al. | |
| 5,443,832 A | 8/1995 | Amerongen et al. | |
| 5,603,943 A | 2/1997 | Yanagawa et al. | |
| 5,885,586 A | 3/1999 | Eckhardt et al. | |
| 5,985,287 A | 11/1999 | Tan et al. | |
| 5,985,312 A | 11/1999 | Jacob et al. | |
| 6,103,243 A | 8/2000 | Russell-Jones et al. | |
| 6,248,363 B1 * | 6/2001 | Patel et al. | 424/497 |
| 6,328,997 B1 * | 12/2001 | Beckett | 424/686 |
| 6,544,561 B2 * | 4/2003 | Beckett | 424/686 |
| 2002/0068090 A1 | 6/2002 | Bell et al. | |
| 2004/0013695 A1 | 1/2004 | Vande-Velde | |

FOREIGN PATENT DOCUMENTS

| | | |
|---|---|---|
| EP | 0266119 | 5/1988 |
| EP | 0445710 A1 | 9/1991 |
| FR | 2143588 | 2/1973 |
| GB | 1078879 B1 | 8/1967 |
| GB | 2195996 | 4/1988 |
| WO | 91/16072 | 10/1991 |
| WO | 94/09823 | 5/1994 |
| WO | 94/21288 | 9/1994 |
| WO | 9505194 | 2/1995 |
| WO | WO 00/45847 A1 | 8/2000 |
| WO | 02/40676 | 5/2002 |
| WO | 03/096869 | 11/2003 |
| WO | 2004/047794 | 6/2004 |

OTHER PUBLICATIONS

Sinhh et al. Nature Biotechnology, vol. 17, p. 1075-1081.*
Imject Alum Pierce data sheet, 2006, pp. 1-2.*
Costagliola et al. Endocrinology, 1994, vol. 135, p. 2150-2159.*
Khashe et al. Current Microbiology, 1996, vol. 33, p. 104-108.*
Fleming et al. Contact Dermatitis. 1998, vol. 38, p. 337-365.*
Machuca et al. Intervirology 1999, vol. 42 p. 37-42.*
Letvin, 2006, Nature Immunology, vol. 6, p. 930-939.*
Ivory et al. Genetic Vaccines and Therapy, 2004, vol. 2, p. 1-8.*
S. Shima et al., "IgM antibody production in mice intraperitoneally injected with zirconium oxychloride", British Journal of Industrial Medicine 1987; 44:633-637.
S. Denham et al., "Studies on the adjuvant action of beryllium III. The Activity in the plasma of lymph efferent from nodes stimulated with beryllium", Immunology 1988; 64:341-344.

(Continued)

*Primary Examiner*—Zachariah Lucas
*Assistant Examiner*—Agnieszka Boesen
(74) *Attorney, Agent, or Firm*—Fish & Richardson P.C.

(57) ABSTRACT

Parenteral vaccine formulations and adjuvant compositions comprising certain salts as adjuvants are disclosed. Such parenteral vaccine formulations are used for generating an immune response in a subject following administration of the vaccine formulation or the adjuvant composition. Also disclosed is the use of these salts as adjuvants in parenteral vaccine formulations and adjuvant compositions, and to vaccine adjuvants comprising such salts.

20 Claims, 3 Drawing Sheets

OTHER PUBLICATIONS

J.G. Hall, "Studies on the adjuvant action of beryllium, IV. The preparation f beryllium containing macromolecules that induce immunoblast responses in vivo", Immunology 1998; 64:345-351.

A.J. Aller, "The Clinical Significance of Beryllium" J. Trace Elem. Electrolytes Health Dis. vol. 4, No. 1, 1990, p. 1-6.

Ephraim Shoff et al., "The usefulness of strontium as an adjuvant to calcium in the remineralization of the skeleton in man", Bull. Hosp. Joint DB., 13(1), 59-66, (1952).

Irwin M. Braverman, M.D., "Zirconium: Its effect on the reticuloendotherlial system and action as an immunologic adjuvant", J. Invest. Dermatol43, 509-518., (1964).

Gilligan CA et al, "Oral vaccines: design and delivery", Foreign Medical Sciences (Section of Pharmacy), vol. 19, No. 3, pp. 160-163.

Fanta, C. et al "Systemic Immunological Changes Induced by Administration of Grass Pollen Allergens via the Oral Mucosa during Sublingual Immunotherapy" International Archives of Allergy and Immunology, vol. 120, No. 3, Nov. 1999, pp. 218-224.

Walker, Samantha M. et al, "Grass pollen immunotherapy for seasonal rhinitis and asthma: A randomized controlled trial" Journal of Allergy and Clinical Immunology, vol. 107, No. 1, Jan. 2001, pp. 87-93.

Callahan, P.M. et al. "The Importance of Surface Charge in the Optimization of Antigen-Adjuvant Interactions" Pharmaceutical Research (1991), vol. 8, No. 7, pp. 851-858.

International Search Report for National Application No. 1468/04, dated Jul. 11, 2005.

Ulmer, J.B., et al., "Enhancement of DNA vaccine potency using conventional aluminum adjuvants", Vaccine 2000, vol. 18, pp. 18-28.

McClure, Susan J., et al., "Effects of Adjuvant and Route of Immunization on the Intestinal Immune Response of Sheep to Ovalbumin", Regional Immunology, 1994, vol. 6, pp. 210-217.

Reddin, Karen M., et al., "Comparison of the immunological and protective responses elicited by microencapsulated formulations of the F1 antigen from Yersinia pestis", Vaccine 1998, vol. 16, No. 8, pp. 761-767.

Mirchamsy, Hossein, et al., "Stimulating Role of Toxoids-laden Liposomes in Oral Immunization against Diphtheria and Tetanus Infections", Biologicals (1996) 24, pp. 343-350.

Stahl-Hennig, Christiane, et al., "Immunization with Tween-Ether-Treated SIV Adsorbed onto Aluminum Hydroxide Protects Monkeys against Experimental SIV Infection", Virology (1992), No. 186, pp. 588-596.

Marano, Albert R., et al., "Effect of sucralfate and an aluminum hydroxide gel on gastic emptying of solids and liquids", Clin. Pharmacol. Ther., Jun. 1985, pp. 629-632.

Lockard, Joan S., et al., "Prophylaxis with Diphenylhydantoin and Phenobarbital in Alumina-Gel Monkey Model. I. Twelve Months of Treatment: Seizure, EEG, Blood, and Behavioral Data", Epilepsia (1976), vol. 17, pp. 37-47.

Favaro, Rosa M.D., et al., "Bioavailability of Vitamin A in the Rat Following Ingestion of Neomycin Sulfate or Aluminium Hydroxide", Internat. J. Vit. Nutr. Res. (1994), No. 64, pp. 98-103.

Fadel, H., et al., "Availability of Norethisterone Acetate from Combined Oral Contraceptive Tablets", Pharmazie 34, H.1 (1979).

Taudorf, Ebb, Oral Immunotherapy, Laegeforeningens Forlag, Kobenhavn, 1992, pp. 3-23.

Callahan, et al. "The Importance of Surface Charge in the Optimization of Antigen—Adjuvant Interactions", Pharmaceutical Research, vol. 8, No. 7, 1991. pp. 851-858.

Weast, Robert C., "Nomenclature of Inorganic Chemistry—Coordination Compounds", Handbook Of Chemistry and Physics, 1975-1976 56th Edition. pp. B58-B65.

Abstract of JP 65008152.

Ipsen and Lowenstein. "Isolation and Immunochemical Characterization of the Major Allergen of Birch Pollen (Betual verrucosa)", Journal of Allergy and Clinical Immunology, vol. 72, No. 2, Aug. 1988, pp. 150-159.

Gupta, et al. Chapter 8, pp. 229-276 of Vaccine Design: The Subunit and Adjuvant Approach, ed. Michael F. Powell and Mark J. Newman, Plenum Press, NY 1995.

Local Immunotherapy, EAAC/ESPACI Position Paper by working group on local immunotherapy of the EAACI Immunotherapy Subcommittee and the ESPACI Immunotherapy Committee. Apr. 1998.

Vogel, et al. Chapter 7, pp. 141-228 of Vaccine Design: The Subunit and Adjuvant Approach, ed. Michael F. Powell and Mark J. Newman, Plenum Press, NY 1995.

Singh M; O'Hagan D: "Advances ini Vaccine Adjuvants" Nature Biotechnology, Nature Publishing Group, New York, NY, US, vol. 17, No. 11, Nov. 1, 1999, pp. 1075-1081, XP000999107 ISSN: 1087-0156, *p. 1075; figure 1; table 1*.

J. Y. Lee et al., "Beryllium, an adjuvant that promotes gamma interferon production." Infection and Immunity, vol. 68, No. 7, Jul. 2000, pp. 4032-4039, XP002169720 Washington, US.

Levine L; Stone J L; Wyman L: "Factors Affecting the Efficiency of the Aluminum Adjuvant in Diphtheria and Tetanus Toxoids" Journal of Immunology, American Association of Immunologists, US, vol. 75, No. 4, Oct. 1, 1955, pp. 301-307, XP008064584, ISSN: 0022-1767.

Stas' N F; Konovalova Z S; Marchenko N A: "Modification of Aluminum Hydroxide Used as an Adjuvant" Khimiko-Farmatsevticheskii Zhurnal, Moscow, RU, vol. 65/66, No. 24, Jan. 1, 1990, p. 7, XP008064498 ISSN: 0023-1134 *"Summary"* & Database Biosis Biosciences Information Service, Philadelphia, PA, US; 1990 Stas' N F et al, "Modification of Aluminum Hydroxide Used As An Adjuvant" XP002169722.

Wedrychowicz H; Bezubik B: "Influence of adjuvants on immunity in rabbits vaccinated with infective larval somatic proteins of Trichostronglyus colubriformis" Veterinary Parasitology, Elsevier Science, Amsterdam, NL, vol. 37, No. 3-4, Nov. 1, 1990, pp. 273-284, XP023712333 ISSN: 0304-4017 [retrieved on Nov. 1, 1990] abstract; figure 1; table 1* & Database Biosis Biosciences Information Service, Philadelphia, PA, US; 1990.

* cited by examiner

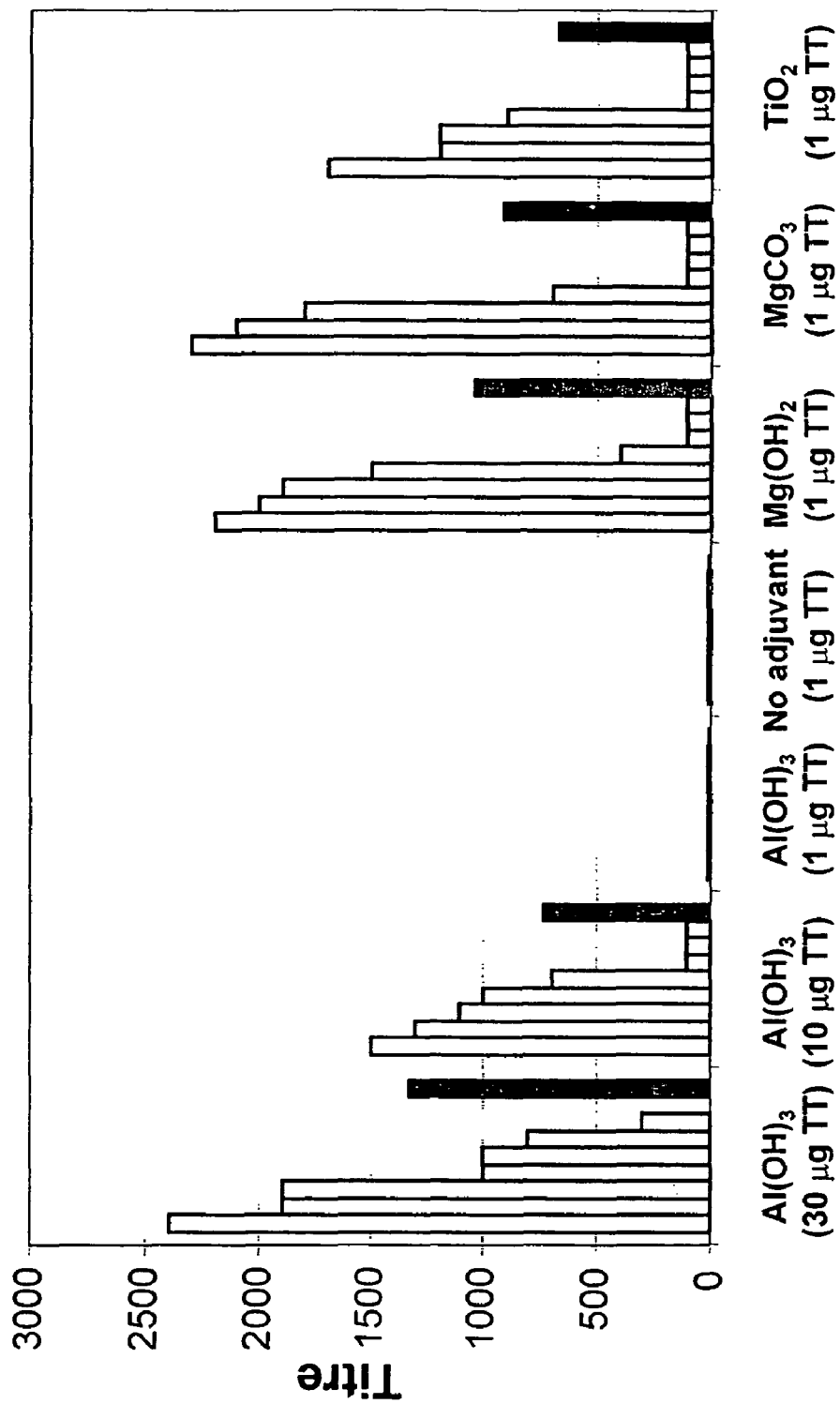
FIGURE 1  TT-specific antibody titre on day 7.

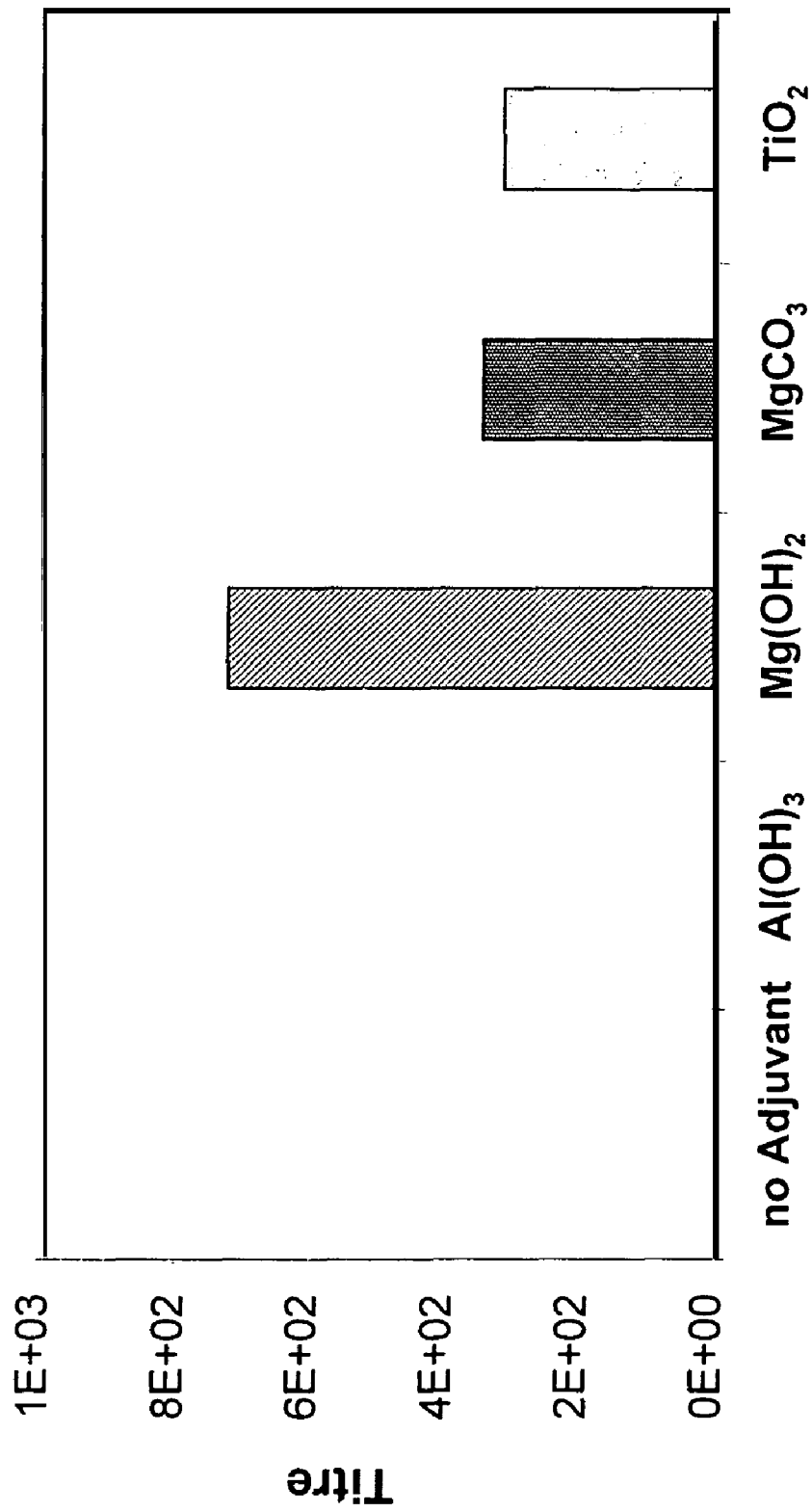

PARENTERAL VACCINE FORMULATIONS AND USES THEREOF

This application is a continuation of U.S. application Ser. No. 09/925,635 filed Aug. 9, 2001, pending, which claims benefit of Provisional U.S. Application No. 60/224,037 filed Aug. 9, 2000, and of Denmark Application No. PA 2000 01194 filed Aug. 9, 2000, each of which is incorporated by reference herein in its entirety.

The present invention concerns the field of parenteral vaccine formulations and adjuvant compositions comprising certain salts as adjuvants. Such novel parenteral vaccine formulations are used for generating an immune response in a subject, including a vertebrate such as a human, following administration of the vaccine formulation. The invention further relates to the use of these salts as adjuvants in parenteral vaccine formulations and adjuvant compositions, and to vaccine adjuvants comprising such salts.

BACKGROUND OF THE INVENTION

Immunological adjuvants are substances that, when administered together with an antigen, have the capacity to augment the immune response to the antigen. When used as a component in a vaccine formulation, the adjuvant improves the immunogenicity of the vaccine in the sense that it will enhance the immune response of the vaccinated subject, thereby reducing the amount of the vaccine component, or reducing the number of administrations needed to induce the desired immune response.

The induced effector immune response may either be of a humoral nature, i.e. an antibody response, or of a cellular nature, i.e. a cytotoxic T-cell response, or the effector response may be a mixture of both. Both cellular and humoral immune responses require help from T helper lymphocytes. Adjuvants that cause inflammation or induce pro-inflammatory cytokines will induce a Type-1 T helper response ($Th_1$) involving production of IL-12, IL-2 and INFγ. These cytokines support induction of cytotoxic T-lymphocyte (CTL) responses, neutrophil inflammation and $Th_1$ antibody responses, such as IgG1 and IgG3. Non-inflammatory adjuvants are more likely to induce a Type-2 helper response ($Th_2$) involving production of the cytokines IL-4, IL-5 and IL-10. These cytokines can down-regulate $Th_1$ responses, and promote induction of $Th_2$ antibodies such as IgE and IgG4 as well as some cellular responses such as eosiniphilia.

Although adjuvants have been applied in the field of immunology and vaccine technology for many years, the underlying mechanisms of action are not completely understood. This has certainly complicated targeted research for identifying new adjuvant candidates.

Several substances have been or are currently being investigated for their adjuvant properties. A few examples are aluminium salts, PLG (polylactide co-glycolide), oil in water emulsions such as MF59 (a squalene in water emulsion), Quil A, Qs-21 and ISCOMs. However, many of the tested adjuvants have several drawbacks, including ineffectiveness with some antigens, contact hypersensitivity, subcutaneous nodules, and granulomatous inflammation. Others still await critical evaluation in clinical trials.

Thus, there is still a strong need for improved or safer adjuvants which can be used in human vaccines.

SUMMARY OF THE INVENTION

It has surprisingly been found that certain salts are particularly suited as adjuvants in vaccine formulations for parenteral administration. Such salts are further particularly suited as components of adjuvant compositions.

Thus, the present invention concerns parenteral vaccine formulations comprising at least one immunogenic substance, and as an adjuvant one or more salts selected from salts formed with a Group 2 element of the Periodic Table selected from Mg, Ca, Sr, Ba and Ra, or a Group 4 element of the Periodic Table selected from Ti, Zr, Hf, and Rf,
and hydrates thereof,
with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine.

The present invention further concerns adjuvant compositions comprising one or more salts selected from salts formed with a Group 2 element of the Periodic Table selected from Mg, Ca, Sr, Ba and Ra, or a Group 4 element of the Periodic Table selected from Ti, Zr, Hf, and Rf,
and hydrates thereof,
with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine.

The present invention also relates to adjuvants comprising such salts.

In further aspects, the present invention concerns the use of the adjuvants and adjuvant compositions as components of vaccine formulations for parenteral administration, the use of such salts as adjuvants in vaccine formulations for parenteral administration, and the use of such salts as components of adjuvant compositions.

The present invention also relates to methods of generating an immune response, which methods comprise administering the vaccine formulations by a parenteral route.

The present invention also enables vaccination or treatment by administration of the vaccine formulation according to the invention.

Furthermore, the present invention relates to a process for preparing the adjuvant compositions and parenteral vaccine formulations of the invention.

BRIEF DESCRIPTION OF THE FIGURES

FIG. 1 shows the results obtained in Example 1 with parenteral vaccine formulations according to the invention. As adjuvant is used magnesium hydroxide, magnesium carbonate hydroxide pentahydrate, or titanium dioxide. As immunogenic substance is used Tetanus toxoid. The results are compared to vaccine formulations either containing aluminium hydroxide as adjuvant, or containing no adjuvant, and as immunogenic substance Tetanus toxoid.

FIGS. 2A and 2B show the results obtained in Example 2 with parenteral vaccine formulations of the invention. As adjuvant is used magnesium hydroxide, magnesium carbonate hydroxide pentahydrate, or titanium dioxide. As immunogenic substance is used Tetanus toxoid. The results are compared to vaccine formulations either containing aluminium hydroxide as adjuvant, or containing no adjuvant, and as immunogenic substance Tetanus toxoid.

DETAILED DESCRIPTION OF THE INVENTION

Figure 2B:
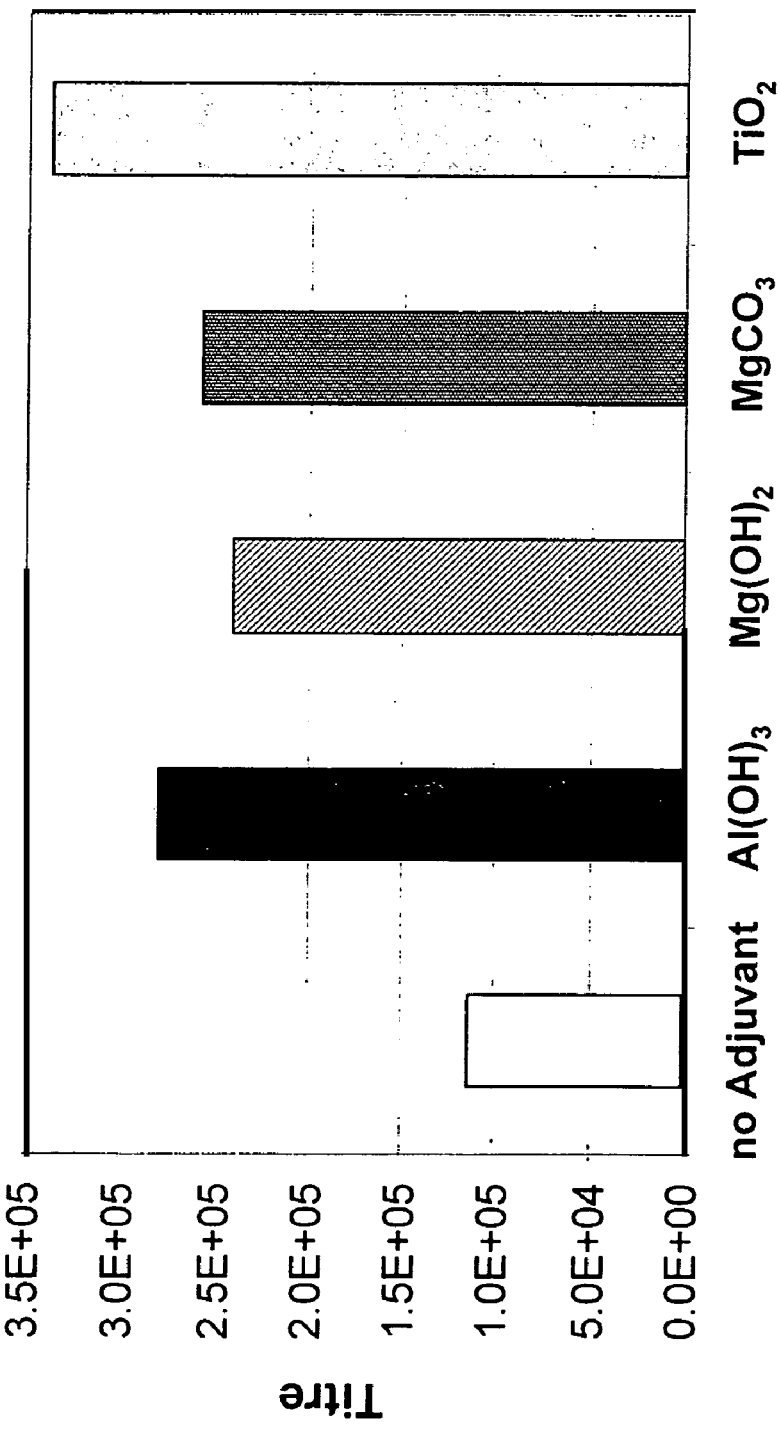

As mentioned above, the mechanisms of action of adjuvants are not completely understood. There are, however, some general theoretical principles by which an adjuvant may exert its effect, namely (1) the adjuvant may create a depot of the antigen resulting in a prolonged slow release over time, thereby reducing the need for booster vaccinations, (2) the adjuvant may enhance antigen uptake by antigen presenting cells (APCs) allowing the antigen to gain access to intracellular antigen processing pathways, and (3) the adjuvant may be pro-inflammatory, i.e. attract and activate macrophages, monocytes, and other cells of the immune system, or stimulate cytokine production.

Furthermore, several other factors relating to adjuvanicity are believed to promote the immunogenicity of antigens. These include (1) rendering antigens particulate, e.g. aluminium salts,
(2) polymers or polymerisation of antigens,
(3) slow antigen release, e.g. emulsions or micro-encapsulation,
(4) bacteria and bacterial products, e.g. CFA,
(5) other chemical adjuvants, e.g. poly-I:C, dextran sulphate and inulin,
(6) cytokines, and
(7) antigen targeting to APC.

While a number of adjuvants (e.g. aluminium salts, PLG, ISCOMs, MF59, MPL, IFA (Freund's incomplete adjuvant), CFA (Freund's complete adjuvant), Quil A, and Qs-21) have been used in experimental and veterinary medicine, aluminium salts (aluminium hydroxide and aluminium phosphate) are currently the only adjuvants used routinely in humans.

Aluminium based vaccines are most commonly manufactured by mixing pre-formed aluminium phosphate or hydroxide gels with the antigen, resulting in adsorption of the antigen to the gel. Aluminium salts are believed to exert their effect as adjuvants by several mechanisms. It is believed that aluminium salts create a depot of antigen at the site of injection, and attract various cells of the immune system, thus creating a local inflammatory environment. Aluminium salts are most likely taken up by antigen presenting cells. Particles of a size of or less than 10 µm are effectively taken up by antigen presenting cells. The particle size of aluminium gels is 0.5-10 µm, making this plausible (see ref. 6).

Although aluminium salts are relatively cheap and easy to manufacture and, in addition, have an excellent track record of safety and adjuvanticity, there are certain problems connected with the use of aluminium compounds. These include local reactions such as erythema, contact hypersensitivity, subcutaneous nodules, and granulomatous inflammation, augmentation of specific and total IgE antibody responses (an undesired antibody type in certain pathogenic conditions such as allergies) in both experimental animals and in humans. In addition, aluminium salts have been reported to be ineffective as adjuvants with some antigens, cf. Gupta et al. (ref. 1).

A disturbing observation has further been reported. It has been suggested in some studies that aluminium can cause experimental degenerative disorders of the central nervous system, cf. Rao et al. (ref. 2). Although there, as yet, is no clinical evidence linking the use of aluminium-containing vaccines to the development of human neuro-degenerative disorders such as Alzheimer's disease, a connection has been postulated and widely debated, cf. Savory et al. (ref. 3). This has generated some anxiety concerning the continuous use of aluminium-containing adjuvants in humans, and the search for alternative, aluminium free adjuvants has been called for.

Also the use of magnesium hydroxide in combination with aluminium hydroxide has been studied. While magnesium hydroxide alone has a low adsorbent activity, it may enhance the activity of aluminium hydroxide as an adjuvant, cf. Stas et al (ref. 8).

Beryllium being the lightest metal with an atomic weight of 4 and a molecular weight of 9 has been known to act as an antigen and further it has been shown to act as an adjuvant promoting the production of IFN- and enhancing the properties of IL-12 in a study on *Leishmania*-susceptible mice, which are immunized with soluble leishmanial antigen. The ability of beryllium to synergize with IL-12 may be an important factor in the development of adjuvants. Accordingly, beryllium has been suggested potential for development as a vaccine adjuvant, cf. Lee et al (ref. 7).

Thus, many adjuvant candidates have been suggested. Many of these promising new adjuvant candidates have, however, failed to pass the developmental stage, because they have been shown to lack one or several of the characteristics desired for adjuvants, when tested in pre-clinical trials, cf. Newman (ref. 4). Many adjuvant candidates have displayed unacceptable levels of toxicity, thus limiting the applicability to very serious conditions, such as chronic viral infection, cancer or HIV therapy, where the use of adjuvants inducing higher levels of local or systemic side effects may be more acceptable. Some of the candidates have proven too costly to manufacture, or the manufacturing and purification process is too complicated to be feasible. Furthermore, a good adjuvant for human use should display physico-chemical stability for longer periods, preferably a year, and some adjuvant candidates have proven to have a limited shelf life.

PLG polymers were initially developed for use as biodegradable surgical sutures, and depot-formulation of various hormones. The characteristics of PLG (biodegradability, documented safety in humans, and relatively easy manufacturing) made it an obvious vaccine delivery candidate. The system is based on encapsulation of the antigen, and, if necessary, other components in 1-100 µm microspheres. When the particle is degraded, the antigen is released. The kinetics of the release can be adjusted by altering the composition of the polymers. Smaller microspheres (≦10 µm) will be taken up by antigen presenting cells, thus targeting the antigen to immunocompetent tissues. The main drawback of the PLG technology is the harsh physical and chemical conditions needed in the manufacturing process, which may render this technology useless with certain labile antigens. Although a good safety profile of PLG has been established, the adjuvanticity of PLG vaccines still awaits critical evaluation in clinical trials, cf. Newman (ref. 4).

Oil in water emulsions such as MF59 (a squalene in water emulsion) are more liquid than water in oil emulsions, and are therefore not intended to form a depot of antigen at the site of injection. Rather, it is believed that the oil in water emulsions exert their adjuvant effect when droplets are taken up by antigen presenting cells, cf. O'Hagan et al. (ref. 5). The emulsion is prepared and subsequently the antigen added, thus making the technology suitable for fragile or labile antigens, or purposes where the retention of the three dimensional structure of the antigen is required, cf. Newman (ref. 4). The potency of MF59 vaccines is reportedly up to 50-fold higher than vaccines delivered as aluminium salt formulations, in a number of animal models, cf. O'Hagan et al. (ref. 5). The MF59 adjuvant reportedly induces an antibody response, rather than a cellular immune response, and is thus better suited for use in vaccines aiming at augmenting or inducing antibody responses, cf. Newman (ref. 4).

Other adjuvant systems such as Quil A, Qs-21 and ISCOMs are based on natural products, namely saponins (sterol and triterpenoid glycosides, derived from the bark of the *Quilaja saponiaria* tree). Quil A is a crude preparation of more than 20 *Quilaja saponins*, and is currently used for veterinary vaccine technology. However, owing to the heterogenecity and toxicity of the product, Quil A is not suitable for use in human vaccines. This lead to further purification of the individual saponins in Quil A. Experimental vaccine and toxicology studies led to the identification of the Qs-21 as the saponin best suited for use in human vaccines, cf. Newman (ref. 4). Both Quil A and Qs-21 can elicit cellular immune responses as well as antigen responses in experimental animals. Qs-21 is currently being tested in clinical trials. ISCOMs (immunostimulatory complexes) are spherical, hollow particles composed of cholesterol, saponin and phospholipid. Vaccine studies in animals have shown that lower doses of saponins are required to induce similar immune responses, when ISCOMs formulations are used. However, ISCOMs are relatively complicated to manufacture, and the advantage over Qs-21 is still debated, cf. Newman (ref. 4).

As evident from the above, there is a need for suitable adjuvants, in particular such suited for human use. There are several key features which an ideal adjuvant candidate should most preferably display, namely (1) Safety. The adjuvant should preferably be sufficient non-toxic and biodegradable, and preferably induce minimal local and systemic reactions.

(2) Potency. The adjuvant should preferably be able to reduce the amount of antigen and/or number of applications needed in order to induce a long-lasting immune response (be it an antibody or cellular response).

(3) Stability. The adjuvant should preferably be stable for longer periods, preferably for more than a year, at 4° C. or room temperature. Also, the manufacturing process should not have any detrimental effect on the antigen.

(4) Manufacturing and costs. The adjuvant should preferably be easy and cheap to manufacture in order not to increase the manufacturing costs of the vaccine tremendously.

The present invention provides adjuvants which fulfil some or all of the above criteria. It has surprisingly been found that certain salts are capable of acting as adjuvants in parenteral vaccine formulations.

Thus, in a first aspect, the present invention relates to parenteral vaccine formulations comprising at least one immunogenic substance, and as an adjuvant one or more salts selected from salts formed with a Group 2 element of the Periodic Table or a Group 4 element of the Periodic Table, and hydrates thereof, with the proviso that the salt is not calcium phosphate.

The advantages of the adjuvant salts are numerous. It has surprisingly been found that these salts act as adjuvants when included in parenteral vaccine formulations, implying that it will in many cases be possible to reduce the amount of immunogenic substance needed to induce an immune response. Moreover, the adjuvanicity of these salts can in some cases induce an immune response with an earlier onset and/or prolonged persistence, when compared to a conventionally used adjuvant. Accordingly, the number of booster vaccinations to obtain and maintain the desired level of immunity may be reduced. Moreover, studies indicate that the use of the salts described herein in vaccine formulations for parenteral use will in some cases increase the magnitude of the immune response, even to greater extents than seen with the conventionally used aluminium hydroxide.

A reason for this could be that the adjuvant salts exert their effect as adjuvants by creating a depot of the immunogenic substance, resulting in a slow and prolonged release of the immunogenic substance over time. On the other hand, the salts could also promote uptake of the immunogenic substance by antigen presenting cells. It should, however, be emphasised that this is a hypothesis, and should therefore have no limiting effect.

The salts can be characterised by a number of physical-chemical properties. These properties are believed to influence the salt's ability to act as an adjuvant to a greater or lesser extent. For instance, the solubility constant, the lattice energy, the nature of binding (covalent binding contra ionic binding), the pH, the oxidation stage, the particle size, and the ability to adsorb the immunogenic substance could all be involved. The compounds listed in the Examples have a low solubility and high lattice energy. Furthermore, the vaccine formulations of the Examples are slightly alkaline. Thus, some of the characteristics may be important in connecting with adjuvanicity. However, it is to be understood that the above are hypothesises and therefore should have no limiting effect on the scope of the invention.

The salts falling within the definition above are known chemical compounds, and some are currently being applied in veterinary or human medicine as laxatives, antacids or in cosmetic applications, cf. the examples in the table below. None of the salts have previously been used in parenteral vaccine formulations as sole adjuvants.

| Name | Compound | Solubility[1] | Current use | Dose[2] |
|---|---|---|---|---|
| Magnesium hydroxide | $Mg(OH)_2$ | Insoluble | Antacid (h), cathartic laxative (v) | 0.5 |
| Magnesium carbonate hydroxide pentahydrate | $(MgCO_3)_4$ $Mg(OH)_2$ $5H_2O$ | Low/ insoluble | Antacid (h), laxative (v) | 0.5 |
| Titanium oxide | $TiO_2$ | Insoluble | Topical protection (h)/ cosmetic applications (h) | 1.0 |

[1]Solubility in water, according to manufacturer
[2]Recommended maximum dose (g per kg bodyweight)
h approved for use in humans
v approved for veterinary use As used herein, the term "adjuvant" refers to an immunological adjuvant. By this is meant a compound that is able to enhance the immune system's response to an immunogenic substance. The term "immunogenic" refers to a substance or active ingredient which when administered to a subject, either alone or with an adjuvant, induces an immune response in the subject. The term "immune response" includes specific humoral, i.e. antibody, as well as cellular immune responses, the antibodies being serologic as well as secretory and pertaining to the subclasses IgM, IgD, IgG, IgA and IgE as well as all isotypes, allotypes, and subclasses thereof. The term is further intended to include other serum or tissue components. The cellular response includes Type-1 and Type-2 T-helper lymphocytes, cytotoxic T-cells as well as natural killer (NK) cells.

The concept of vaccination/immunisation is based on two fundamental characteristics of the immune system, namely specificity and memory. The first vaccination/immunisation will initiate a response specifically directed to the antigen with which the subject was challenged. Furthermore, a population of memory B and T lymphocytes will be induced. Upon re-exposure to the antigen or the pathogen it is derived from, the immune system will be primed to respond much faster and much more vigorously, thus endowing the vaccinated/immunised individual with immunological protection against the pathogen.

It lies within the scope of the present invention to use one or more immunogenic substances in the vaccine formulation. A case where the vaccine comprises more than one immunogenic substance is the so-called combination vaccines.

Examples of immunogenic substances are antigens, allergens, allergoids, peptides, proteins, haptens, carbohydrates, peptide nucleic acids (PNAs, a sort of synthetic genetic mimic), and viral or bacterial material as well as analogues or derivatives thereof. In the present context, the term "analogues or derivatives" is intended to include modified forms of the immunogenic substance. The modification can be made by chemical modification or synthetic modification, e.g. by PEGylation (PEG=polyethylene glycol), biotinylation, deamination, maleination, substitution of one or more amino acids, by cross-linking, by glycosylation, or by other recombinant or synthetic technology. The term is also intended to include natural-occurring mutations, isoforms and retroinverse analogues.

In particular such immunogenic substances may be natural, recombinant or modified proteins or fragments thereof, antigens, allergens, allergoids, peptides, haptens conjugated on a suitable carrier like KLH (hey hole limpet hemocyanin) or Tetanus toxoid, carbohydrates, optionally inactivated or attenuated bacteria or virus as well as components thereof, RNA, DNA, PNA, parasites or retroviruses, parasitic material, mycoplasma, or toxins, e.g. such derived from Tetanus toxoid, Diphtheria toxoid, Cholera toxin A and B subunits, Rubella, Rhabdovirus (rabies), Myoxoviruses, Paramyoxyviruses like parainfluenza virus, mumps and measles, Picornaviruses like poliovirus, coxsackievirus, echovirus and rhinovirus, Reoviruses, Poxviruses like small pox virus, Vaccinia virus and cowpox virus, Papovaviruses like polyoma virus, papilloma virus and SV-40, Adenoviruses, EBV like mononucleosis virus, Parvoviruses like HPV B19, Herpes viruses like Herpes simplex virus, and Herpes zoster virus (Varicella virus), Cytomegalovirus (CMV), Arboviruses like yellow fever and Dengue fever, Retroviruses like HIV, Hepatitis viruses like Hepatitis A, Hepatitis B and Hepatitis C, Haemophilius influenzae type B, *Mycobacterium* like *M. tuberculosis, M. bovis, M. africanum, M. microti, M. avium, M. intracellulare, M. kansasii, M. gordonae, M. paratuberculosis*, and *M. lepramurium, Borrelia* spp. like *B. burgdorferi*, in particular *B. burgdorferi* sensu lato and *B. burgdorferi* sensu stricto, *B. garinii, B. afzelii, B. duttoni* and *B. recurrentis, Bordetella pertussis* (whooping cough), *Salmonella* spp. like *S. typhimurium* and *S. typhi, Treponema* spp. like *T. pallidum, Leptospira* spp., *Campylobacter* spp. like *C. jejuni, Helicobacter* spp. like *H. pylori, Pseudomonas* spp., *Legionella* spp., *Neisseria* spp. like *N. gonorrhoea* and *N. menigitidis, Chlamydia* spp. like *C. trachomatis, C. pneumonia* and *C. psittae, Enterobacter* spp., *Klebsiella* spp., *Yersinia* spp., *Vibrio* spp. like *Vibrio cholerae, Gardnerella* spp., *Rickettsia* spp., *Clostridium* spp. like *C. difficile, C. botulinum* and *C. tetani, Lactobacillus* spp., *Listeria* spp., and *Mycoplasma* spp. like *M. pneumoniae M. hominis, Plasmodium falciparum*, and *Leishmania donovani,* moulds and fungi such as *Clahdosporium, Alternaria, Aspergillus, Besidiomycetes, Candida albicans*, and *Penicillinum,* allergoids such as glutaraldehyde or PEG modified allergen complexes.

Examples of immunogenic substances used in combination vaccines are immunogenic substances involved with Diphteria-Tetanus-Wooping cough-Polio, Measles-Parotitis-Rubella, and Hepatitis A and B.

Non-limiting examples of allergens to be used in the parenteral vaccine of the invention include inhalation allergens originating i.a. from trees, grasses, herbs, fungi, house dust mites, storage mites, cockroaches and animal hair, feathers, and dandruff. Important pollen allergens from trees, grasses and herbs are such originating from the taxonomic orders of Fagales, Oleales and Pinales including i.a. birch (*Betula*), alder (*Alnus*), hazel (*Corylus*), hornbeam (*Carpinus*) and olive (*Olea*), the order of Poales including i.a. grasses of the genera *Lolium, Phleum, Poa, Cynodon, Dactylis* and *Secale*, the orders of Asterales and Urticales including i.a. herbs of the genera *Ambrosia* and *Artemisia*. Important inhalation allergens from fungi are i.a. such originating from the genera *Alternaria* and *Cladosporium*. Other important inhalation allergens are those from house dust mites of the genus *Dermatophagoides*, storage mites from the genus *Lepidoglyphys* destructor, those from cockroaches and those from mammals such as cat, dog, horse, cow, and bird. Further, allergens to be used may be derived from venom allergens including such originating from stinging or biting insects such as those from the taxonomic order of Hymenoptera including bees, wasps, and ants.

It is to be understood that the term derived from includes the naturally-occurring substance as well as isoforms thereof. Furthermore, the substance may be prepared by means of recombinant or synthetic techniques. Specific allergen components are known to the person skilled in the art and include e.g. Bet v 1 (*B. verrucosa*, birch), Aln g 1 (*Alnus glutinosa*, alder), Cor a 1 (*Corylus avelana*, hazel) and Car b 1 (*Carpinus betulus*, hornbeam) of the Fagales order. Others are Cry j 1 (Pinales), Amb a 1 and 2, Art v 1 (Asterales), Par j 1 (Urticales), Ole e 1 (Oleales), Ave e 1, Cyn d 1, Dac g 1, Fes p 1, Hol l 1, Lol p 1 and 5, Pas n 1, Phl p 1 and 5, Poa p 1, 2 and 5, Sec c 1 and 5, and Sor h 1 (various grass pollens), Alt a 1 and Cla h 1 (fungi), Der f 1 and 2, Der p 1 and 2 (house dust mites, *D. farinae* and *D. pteronyssinus*, respectively), Lep d 1, Bla g 1 and 2, Per a 1 (cockroaches, *Blatella germanica* and *Periplaneta americana*, respectively), Fel d 1 (cat), Can f 1 (dog), Equ c 1, 2 and 3 (horse), Apis m 1 and 2 (honeybee), Ves g 1, 2 and 5, Pol a 1, 2 and 5 (all wasps) and Sol i 1, 2, 3 and 4 (fire ant).

As specified above, the salts to be used as adjuvants in the vaccine formulations for parenteral use is such formed with a Group 2 or Group 4 element of the Periodic Table, i.e. salts formed with Mg, Ca, Sr, Ba, Ra, Ti, Zr, Hf, or Rf. Here it is to be understood that the salts are composed of a cationic part and an anionic part. The Group 2 or Group 4 elements constitute the cationic part.

The salts to be used may be so-called double salts. Hydrates, e.g. mono-, di-, tri-, tetra- and pentahydrates, of the salts also lies within the scope of the invention. Di- or trications (e.g. tricalcium) are also part of the scope of the invention. Di- or trianions (e.g. disulphate) are also a part of the scope of the invention.

The salt may be an organic salt or an inorganic salt.

When the salt is an organic salt, examples of anion part are acetates, oxalates, citrates, and tartrates.

The salt to be used in the present invention is preferably an inorganic salt.

In an embodiment, the parenteral vaccine formulation according to the invention is such, wherein the adjuvant is selected from salts formed with oxides, peroxides, hydroxides, carbonates, phosphates, pyrophosphates, hydrogenphosphates, dihydrogenphosphates, sulphates, and silicates, and hydrates thereof, however having regard to the proviso above.

In another embodiment, the parenteral vaccine formulation is such, wherein the adjuvant is selected from salts formed between Mg, Ca, Ba, Ti, or Zr, and oxide, peroxide, hydroxide, and/or carbonate, and hydrates thereof.

In a particular embodiment, the parenteral vaccine formulation of the invention is such, wherein the adjuvant is selected from salts formed between magnesium and oxide, peroxide, hydroxide, and/or carbonate, calcium and oxide, peroxide, hydroxide, and/or carbonate, barium and oxide, peroxide, hydroxide, and/or carbonate, titanium and oxide, peroxide, hydroxide, and/or carbonate, and zirconium and oxide, peroxide, hydroxide, and/or carbonate, and hydrates thereof.

In a preferred embodiment, the parenteral vaccine formulation of the invention is such, wherein the adjuvant is selected from magnesium hydroxide, magnesium carbonate hydroxide pentahydrate, titanium dioxide, calcium carbonate, barium hydroxide, barium peroxide, barium carbonate, barium sulphate, beryllium oxide, calcium sulphate, calcium silicate, dicalcium silicate, tricalcium silicate, calcium pyrophosphate, calcium peroxide, calcium hydroxide, tricalcium phosphate, calcium hydrogenphosphate, calcium dihydrogenphosphate, calcium sulphate dihydrate, magnesium carbonate, magnesium oxide, magnesium dioxide, magnesium sulphate, trimagnesium phosphate, magnesium silicate, dimagnesium trisilicate, magnesium trisilicate, titantium disulphate, zirconium dioxide, zirconium hydroxide, zirconium sulphate, strontium peroxide, and strontium carbonate.

The parenteral vaccine formulation of the invention is preferably such, wherein the adjuvant is selected from magnesium hydroxide, magnesium carbonate hydroxide pentahydrate, and titanium dioxide.

In an embodiment, the adjuvant is selected so as to comprise one or more salts having a low solubility and/or high lattice energy.

In some cases, the parenteral vaccine formulation according to the invention may further comprise an additional adjuvant. Such additional adjuvant is selected from conventionally used adjuvants. Examples of such additional adjuvants include saponins such as Quil A and Qs-21, oil in water emulsions such as MF59, MPL, PLG, PLGA, aluminium salts, calcium phosphate, water in oil emulsions such as IFA (Freund's incomplete adjuvant) and CFA (Freund's complete adjuvant), interleukins such as IL-1β, IL-2, IL-7, IL-12, and INFγ, Adju-Phos®, glucan, antigen formulation, Cholera Holotoxin, liposomes, DDE, DHEA, DMPC, DMPG, DOC/Alum Complex, ISCOMs®, muramyl dipeptide, monophosphoryl lipid A, muramyl tripeptide, and phospatidylethanolamine (see also "Vaccine Design. The Subunit and Adjuvant Approach", Chapter 7 (ref. 6)). In a preferred embodiment, the additional adjuvant is selected from saponins such as Quil A and Qs-21, MF59, MPL, PLG, PLGA, calcium phosphate, and aluminium salts.

Furthermore, the parenteral vaccine formulation of the invention may suitably comprise one or more pharmaceutically acceptable excipients and carriers. Examples of such are diluents, buffers, suspending agents, wetting agents, solubilising agents, pH-adjusting agents, dispersing agents, preserving agents, and/or colorants.

The vaccine formulation of the inventions is administered by a parenteral route. The parenteral route includes intravenous, intramuscular, intraarticular, subcutaneous, intradermal, epicutantous/transdermal, and intraperitoneal administration.

The cation of the adjuvant salt is preferably present in the vaccine in an amount of from about 0.0004 to about 120 M, such as from about 0.004 to about 12 M, preferably from about 0.008 to about 6 M.

The amount of the additional adjuvant depends on the adjuvant and the immunogenic substance in question, and will be the subject to optimisation. However, the person skilled in the art will readily know how to optimise the amount of such additional adjuvant having regard to the other constituents to be included in the formulation.

In one embodiment of the parenteral vaccine formulation, the adjuvant is magnesium hydroxide. In another embodiment of the parenteral vaccine formulation, the adjuvant is magnesium carbonate hydroxide pentahydrate. In a third embodiment of the parenteral vaccine formulation, the adjuvant is titanium dioxide. In a fourth embodiment of the parenteral vaccine formulation, the adjuvant is a combination of magnesium hydroxide and magnesium carbonate hydroxide pentahydrate, magnesium hydroxide and titanium dioxide, or magnesium carbonate hydroxide pentahydrate and titanium dioxide. In a fifth embodiment, the adjuvant is a combination of magnesium hydroxide, magnesium carbonate hydroxide pentahydrate, and titanium oxide. Such parenteral vaccine formulations may also suitably comprise an additional adjuvant. Such additional adjuvants are selected from those indicated above. However, the additional adjuvant is preferably selected from saponins such as Quil A and Qs-21, MF59, MPL, PLG, PLG A, calcium phosphate, and aluminium salts.

Furthermore, it may be possible to manufacture vaccine formulations having combined characteristics such as earlier onset, prolonged persistence, increased potency, $Th_1$, $Th_2$ and/or cytotoxic response depending on the choice of adjuvants or combination of adjuvants. Thus, it could be beneficial to use different adjuvant schemes depending on the type of vaccination. For instance, an adjuvant providing an early onset may be used for the initial vaccination, and an adjuvant providing enhanced potency may be used for boosters. For this purpose, a combination of the adjuvants described herein may be very suitable.

By including an additional adjuvant, it may be possible to prepare vaccine formulations with further specific or enhanced properties. For instance, addition of MPL may result in a formulation that predominantly induces a $Th_1$ type immune response, whereas addition of saponins may result in a formulation that induces a $Th_1$ type immune response as well as a cytotoxic response. Furthermore, a combination of one or more adjuvant salts in the parenteral vaccine formulations of the invention and one or more additional adjuvants may enable an advantageous combined adjuvant effect, possibly enabling the modulation of $Th_1$, $Th_2$ and/or cytotoxic response(s).

In another aspect, the present invention relates to adjuvant compositions for parenteral use comprising one or more salts selected from salts formed with a Group 2 element of the Periodic Table selected from Mg, Ca, Sr, Ba and Ra, or a Group 4 element of the Periodic Table selected from Ti, Zr, Hf, and Rf, and hydrates thereof, with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine.

Although the salt may be an organic or an inorganic salt, cf. above, the adjuvant composition of the invention is preferably such, wherein the salt is selected from inorganic salts.

In a preferred embodiment, the adjuvant composition is such, wherein the salt is selected from salts formed with oxides, peroxides, hydroxides, carbonates, phosphates, pyrophosphates, hydrogenphosphates, dihydrogenphosphates, sulphates, and/or silicates, and hydrates thereof, however having regard to the proviso above.

As mentioned above, double salts are also part of the present invention. Salts having di- or tri-cations or -anions are also part of the invention.

In particular, the adjuvant composition is such, wherein the salt is selected from salts formed between Mg, Ca, Ba, Ti, or Zr, and oxide, peroxide, hydroxide, and/or carbonate, and hydrates thereof, however, having regard to the proviso above.

The adjuvant composition may particularly be such, wherein the salt is selected from salts formed between magnesium and oxide, peroxide, hydroxide, and/or carbonate, calcium and oxide, peroxide, hydroxide, and/or carbonate, barium and oxide, peroxide, hydroxide, and/or carbonate, titanium and oxide, peroxide, hydroxide, and/or carbonate, and zirconium and oxide, peroxide, hydroxide, and/or carbonate, and hydrates thereof.

In a special embodiment, the adjuvant composition is such, wherein the salt is selected from magnesium hydroxide, magnesium carbonate hydroxide pentahydrate, titanium dioxide, calcium carbonate, barium hydroxide, barium peroxide, barium carbonate, barium sulphate, beryllium oxide, calcium sulphate, calcium silicate, dicalcium silicate, tricalcium silicate, calcium pyrophosphate, calcium peroxide, calcium hydroxide, tricalcium phosphate, calcium hydrogenphosphate, calcium dihydrogenphosphate, calcium sulphate dihydrate, magnesium carbonate, magnesium oxide, magnesium dioxide, magnesium sulphate, trimagnesium phosphate, magnesium silicate, dimagnesium trisilicate, magnesium trisilicate, titantium disulphate, zirconium dioxide, zirconium hydroxide, zirconium sulphate, strontium peroxide, and strontium carbonate.

Preferably, the adjuvant composition is such, wherein the salt is selected from magnesium hydroxide, magnesium carbonate hydroxide pentahydrate, and titanium dioxide.

In some cases, it may be advantageous to include an additional adjuvant in the adjuvant composition. Thus, in one embodiment, the adjuvant composition of the invention further comprises an additional adjuvant. The additional adjuvant may suitably be selected from those mentioned above. In a preferred embodiment, the additional adjuvant is selected from saponins such as Quil A and Qs-21, MF59, MPL, PLG, PLG A, calcium phosphate, and aluminium salts.

The adjuvant composition of the invention may further comprise pharmaceutically acceptable excipients and/or carriers.

Furthermore, the adjuvant composition may comprise diluents, buffers, suspending agents, solubilising agents, pH-adjusting agents, dispersing agents, and/or colorants.

In the adjuvant composition of the invention which may be available as a powder or a gel or suspension, the cation of the salt may suitable be present in an amount of from about 0.0004 to about 120 M, such as from about 0.004 to about 12 M, preferably from about 0.008 to about 6 M.

In one embodiment of the adjuvant composition, the salt is magnesium hydroxide. In another embodiment of the adjuvant composition, the salt is magnesium carbonate hydroxide pentahydrate. In a third embodiment of the adjuvant composition, the salt is titanium dioxide. In a fourth embodiment of the adjuvant composition, the salt is a combination of magnesium hydroxide and magnesium carbonate hydroxide pentahydrate, magnesium hydroxide and titanium dioxide, or magnesium carbonate hydroxide pentahydrate and titanium dioxide. In a fifth embodiment, the salt is a combination of magnesium hydroxide, magnesium carbonate hydroxide pentahydrate and titanium dioxide. Such adjuvant composition may suitably comprise an additional adjuvant. Such additional adjuvants are suitably selected from those indicated above. In a preferred embodiment, the additional adjuvant selected from saponins such as Quil A and Qs-21, MF59, MPL, PLG, PLG A, calcium phosphate and aluminium salts.

In another embodiment, the salt(s) is (are) selected so as to have a low solubility and/or high lattice energy.

In a third aspect, the present invention relates to adjuvants comprising one or more salts selected from salts formed with a Group 2 element of the Periodic Table selected from Mg, Ca, Sr, Ba and Ra, or a Group 4 element of the Periodic Table selected from Ti, Zr, Hf, and Rf, and hydrates thereof, with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine.

The adjuvant of the invention may comprise organic and/or inorganic salts.

In a preferred embodiment of the adjuvant of the invention, the salt is selected from inorganic salts.

The adjuvant of the invention may suitably be such, wherein the salt is selected from salts formed with oxides, peroxides, hydroxides, carbonates, phosphates, pyrophosphates, hydrogenphosphates, dihydrogenphosphates, sulphates, and silicates, and hydrates thereof, however having regard to the proviso above.

In particular the adjuvant may be such, wherein the salt is selected from salts formed between Mg, Ca, Ba, Ti, or Zr, and oxide, peroxide, hydroxide, and/or carbonate, and hydrates thereof.

Particularly interesting adjuvants are such, wherein the salt is selected from salts formed between magnesium and oxide, peroxide, hydroxide, and/or carbonate, calcium and oxide, peroxide, hydroxide, and/or carbonate, barium and oxide, peroxide, hydroxide, and/or carbonate, titanium and oxide, peroxide, hydroxide, and/or carbonate, and zirconium and oxide, peroxide, hydroxide, and/or carbonate, and hydrates thereof.

In one embodiment of the adjuvant of the invention, the salt is selected from magnesium hydroxide, magnesium carbonate hydroxide pentahydrate, titanium dioxide, calcium carbonate, barium hydroxide, barium peroxide, barium carbonate, barium sulphate, beryllium oxide, calcium sulphate, calcium silicate, dicalcium silicate, tricalcium silicate, calcium pyrophosphate, calcium peroxide, calcium hydroxide, tricalcium phosphate, calcium hydrogenphosphate, calcium dihydrogenphosphate, calcium sulphate dihydrate, magnesium carbonate, magnesium oxide, magnesium dioxide, magnesium sulphate, trimagnesium phosphate, magnesium silicate, dimagnesium trisilicate, magnesium trisilicate, titantium disulphate, zirconium dioxide, zirconium hydroxide, zirconium sulphate, strontium peroxide, and strontium carbonate.

In a preferred embodiment, the adjuvant is such, wherein the salt is selected from magnesium hydroxide, magnesium carbonate hydroxide pentahydrate, and titanium dioxide, or the salt is selected from a combination of magnesium hydroxide and magnesium carbonate hydroxide pentahydrate, magnesium hydroxide and titanium dioxide, magnesium carbonate hydroxide pentahydrate and titanium dioxide, or magnesium hydroxide, magnesium carbonate hydroxide pentahydrate, and titanium dioxide.

In a fourth aspect, the present invention relates to the use of a salt formed with a Group 2 element of the Periodic Table selected from Mg, Ca, Sr, Ba and Ra, or a Group 4 element of the Periodic Table selected from Ti, Zr, Hf, and Rf,
and hydrates thereof,
as an adjuvant in a vaccine formulation for parenteral administration,
with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine,
and to the use of a salt formed with a Group 2 element of the Periodic Table selected from Mg, Ca, Sr, Ba and Ra, or a Group 4 element of the Periodic Table selected from Ti, Zr, Hf, and Rf,
and hydrates thereof,
as a component of an adjuvant composition,
with the proviso that the salt is not calcium phosphate, is not magnesium hydroxide in combination with aluminium hydroxide or aluminium oxide and is not calcium hydroxide in gel combination with zinc hydroxide, lecithin and polyalphaolefine.

It lies within the scope of the invention to use the salts separately or in combination. The use of double salts also lies within the scope of the present invention as does the use of di- and tri-cationic or anionic salts.

The salt may be an organic or an inorganic salt, but preferably a salt selected from inorganic salts is used.

In particular, the salt to be used is selected from salts formed with oxides, peroxides, hydroxides, carbonates, phosphates, pyrophosphates, hydrogenphosphates, dihydrogenphosphates, sulphates, and silicates,
and hydrates thereof.

In one embodiment, the salt to be used is selected from salts formed between Mg, Ca, Ba, Ti, or Zr, and oxide, peroxide, hydroxide, and/or carbonate,
and hydrates thereof.

In another embodiment, the salt to be used is selected from salts formed between
magnesium and oxide, peroxide, hydroxide, and/or carbonate,
calcium and oxide, peroxide, hydroxide, and/or carbonate,
barium and oxide, peroxide, hydroxide, and/or carbonate,
titanium and oxide, peroxide, hydroxide, and/or carbonate, and
zirconium and oxide, peroxide, hydroxide, and/or carbonate,
and hydrates thereof.

In a special embodiment, the salt to be used is selected from magnesium hydroxide, magnesium carbonate hydroxide pentahydrate, titanium dioxide, calcium carbonate, barium hydroxide, barium peroxide, barium carbonate, barium sulphate, calcium sulphate, tricalcium silicate, calcium pyrophosphate, calcium peroxide, calcium hydroxide, tricalcium phosphate, calcium hydrogenphosphate, calcium dihydrogenphosphate, calcium sulphate dihydrate, magnesium carbonate, magnesium sulphate, trimagnesium phosphate, magnesium silicate, magnesium trisilicate, titantium disulphate, zirconium sulphate, strontium peroxide, and strontium carbonate.

In a currently preferred embodiment, the salt to be used is selected from magnesium hydroxide, magnesium carbonate hydroxide pentahydrate, and titanium dioxide, or a combination of magnesium hydroxide and magnesium carbonate hydroxide pentahydrate, magnesium hydroxide and titanium dioxide, magnesium carbonate hydroxide pentahydrate and titanium dioxide, or magnesium hydroxide, magnesium carbonate hydroxide pentahydrate, and titanium dioxide.

In a fifth aspect, the present invention relates to methods of generating an immune response in a subject, which methods comprise administering to the subject a parenteral vaccine formulation of the invention.

In a sixth aspect, the present invention enables the vaccination or treatment of a vertebrate including a human being comprising administering to the subject a vaccine formulation of the invention.

As described above, the parenteral vaccine compositions of the present invention comprise at least one immunogenic substance. Thus, the inclusion of two, three, four, five, six or more immunogenic substances are contemplated and believed to be advantageous in some cases. The amount of immunogenic substance(s) depends on the immunogenic substance or combination of immunogenic substances in question. However, it is contemplated that the amount of immunogenic substance required to induce an immune response can, in some cases, be reduced due to the beneficial effects of the adjuvant salts. Thus, the amount of each immunogenic substance will typically be in the range of from 0.0001 to 100000 μg/dose, such as from 0.01 to 10000 μg/dose, from 0.1 to 1000 μg/dose, or from 1 to 100 μg/dose.

The administration of the vaccine formulation of the invention may be as single doses or as several doses. In certain cases, administration only once may be sufficient. In general, several doses should be given with intervals of a day, a week, two weeks, a month, or several months, etc. For example, a single dose may be given once, or a dose may be given as a primer, followed by one or more booster vaccinations, or a continuous vaccination regime like up to four doses per week, followed by one month without vaccinations, followed by up to four doses per week (optionally with increasing amount of immunogen), etc. Optionally different adjuvants or combination of adjuvants may be used in the different vaccinations. These are all examples, and the optimal vaccination regime depends on the immunogenic substance in question and several other factors. The person skilled in the art will readily know how to optimise this.

The adjuvant compositions of the invention can be prepared by forming a suspension or gel of the adjuvant salts by adding liquid, optionally containing buffer, other salts, solvents or excipients, to a dry form of the salt, or, alternatively, adding liquid optionally containing buffer, other salts, excipients, to a pre-equilibrated pre-formed gel of the adjuvant salts. The adjuvant composition may then be formulated to a vaccine formulation with desired immunogenic substance(s) by mixing the adjuvant composition with the immunogenic substance(s), and, if necessary, leaving them to equilibrate before filling. The adjuvant composition and the immunogenic substance(s) may alternatively be mixed in a more concentrated form, thereby enabling later dilution.

Thus in a seventh aspect, the present invention relates to a process for preparing a parenteral vaccine formulation according to the invention, which process comprises adding liquid to a dry form of or a pre-formed gel of a salt formed with a Group 2 element of the Periodic Table selected from Mg, Ca, Sr, Ba and Ra, or a Group 4 element of the Periodic Table selected from Ti, Zr, Hf, and Rf, the salt not being calcium phosphate, not being magnesium hydroxide in combination with aluminium hydroxide or aluminium oxide and not being calcium hydroxide in gel combination with zinc hydroxide, lecithin and polyalphaolefine, thereby obtaining an adjuvant composition, and mixing said adjuvant composition with one or more immunogenic substances and optionally pharmaceutically acceptable carriers and/or excipients, thereby obtaining the parenteral vaccine formulation.

In an eighth aspect, the present invention relates to parenteral vaccine formulations obtainable by the process defined above.

Containers for mixing and storage of the adjuvant compositions and vaccine formulations of the invention may be made of glass or various polymeric materials. The containers chosen should not adsorb the product stored. The containers may suitably be ampoules or capped vials for mono- or multidosage.

The invention is further illustrated by the following non-limited examples.

EXAMPLES

Below, the procedures and protocols applied in carrying out the experiments of Examples 1 and 2 are described in general.

Immunogenic Substance:

Tetanus toxoid (TT) containing 3.0 mg protein/ml, (obtained from Statens Serum Institut, DK-2300 Copenhagen S, Denmark). Vaccine formulations containing aluminium hydroxide, as an adjuvant, contained either 30 µg, 10 µg or 1 µg TT per dose (300 µg/ml, 100 µg/ml, and 10 µg/ml, respectively), and vaccine formulations of the invention containing magnesium hydroxide, magnesium carbonate hydroxide pentahydrate or titanium dioxide, as an adjuvant of the invention, and the adjuvant free vaccine formulation (termed "no adjuvant") all contained 1 µg TT per dose (10 µg/ml).

Adjuvants:

The molar concentration stated below are for the final vaccine formulations:

Aluminium hydroxide, Al(OH)$_3$ 0.045-0.05 M Al$^{3+}$ (1.25 mg Al$^{3+}$/ml). Prepared from Alhydrogel 1.3%® (Superfos, DK-2950 Vedbæk, Denmark).

Magnesium hydroxide, Mg(OH)$_2$ 0.05 M Mg$^{2+}$. Prepared from Mg(OH)$_2$ gel (Reheis, USA).

Magnesium carbonate hydroxide pentahydrate, (MgCO$_3$)$_4$Mg(OH)$_2$5H$_2$O, 0.05 M Mg$^{2+}$. Prepared from Magnesium carbonate hydroxide pentahydrate (Sigma USA).

Titanium dioxide, TiO$_2$, 0.05 M Ti$^{4+}$. Prepared from Titanium dioxide pigment (Kemira, Finland).

Preparation of the Vaccine Formulations:

The vaccine formulations were prepared as follows:

TT was dissolved or diluted to a concentration 10 times that of the concentration in the final vaccine formulation. The adjuvant was dissolved or diluted to a concentration five times that of the concentration in the final vaccine formulation, with regard to the cation. 1 volume TT solution was slowly mixed with 2 volumes adjuvant, and left stirring over night at 4° C. The following day 7 volumes Coca 0.0 buffer (0.25% sodium hydrogen carbonate and 0.5% sodium chloride) was slowly added. The adjuvant free vaccine was prepared as above, with the modification that the adjuvant was substituted with Coca 0.0 buffer.

Immunisations:

For each vaccine formulation, groups of 8 female BALB/Ca mice, 6-8 weeks of age, were given subcutaneous immunisations, inguinally, on days 0 and 14. Each immunisation consisted of 100 µl vaccine.

Blood samples were drawn from the retro orbital vein every 7 days, starting on day 0. Serum was separated from the blood sample, and stored at −20° C., until analysed.

Analysing Serum Samples:

Serum samples were analysed for the presence of TT-specific immune response by means of a direct enzyme linked immunosorbent assay (ELISA), measuring TT-specific antibodies of the IgG class. Briefly, immunosorbent plates (Nunc Maxisorp®, Nunc, Denmark) were coated in a well known manner with TT, and free binding sites were blocked with bovine serum albumin. Serial dilutions of serum samples from the immunised mice were then added onto the plate, together with serial dilutions of a negative control serum pool from unimmunised BALB/Ca mice. A monoclonal TT-specific antibody (obtained from Statens Serum Institut, Copenhagen, Denmark), added in serial dilutions served both as a positive control, as well as an internal standard, used for determining the titre. All samples were added in duplicate.

Bound antibodies were detected by serial incubations of the plate with a biotinylated, polyclonal antiserum to mouse IgG (obtained from Jackson Laboratories, Bar Harbour, Me., USA) followed by a streptavidine-horseradish peroxidase conjugate (obtained from DAKO A/S, Glostrup, Denmark). The plates were developed for 20 minutes with 100 µl ready-made TMB substrate (Kem-En-Tech, Denmark) per well, and the reaction as stopped with an equal volume of 1M H$_2$SO$_4$.

The developed colour reaction was measured as absorption at 450 nm.

Data Analysis:

The absorption at 450 nm was plotted against the dilution of the serum, for each individual mouse, as well as the geometric mean for individual groups.

The strength of the TT-specific antibody response in each serum sample was measured as an arbitrary titre, determined as the serum dilution giving an absorption signal equal to 50% of that obtained with a 3000 fold dilution of the TT-specific monoclonal antibody. Mice that did not respond, i.e., whose responses were indistinguishable from those seen with the serum pool from unimmunised control mice, were assigned a titre of 10. Mice that responded, but with responses below the magnitude required to determine a titre, were assigned a titre of 100.

Example 1

One Immunisation with Vaccine Formulations of the Invention Comprising Either Magnesium Hydroxide, Magnesium Carbonate Pentahydrate, or Titanium Dioxide as an Adjuvant The vaccines were prepared as described above, and the mice were immunised once on day 0 as described above. Blood was drawn on day 7, and serum was prepared and analysed as described above.

In FIG. 1, the results are depicted as titres for individual mice, as well as the mean titre for each group. The adjuvant given is indicated below each group. The number in parenthesis indicates the amount (in μg) of immunogen (TT) given.

As can be seen from FIG. 1, vaccine formulations comprising either magnesium hydroxide, magnesium carbonate pentahydrate, or titanium dioxide as an adjuvant, were more potent at inducing TT-specific antibodies, than vaccine formulation containing Al(OH)$_3$ as an adjuvant. Induction of TT-specific antibodies using an Al(OH)$_3$-containing vaccine formulations required 10-30 times as much immunogen (TT) as vaccine formulations comprising either magnesium hydroxide, magnesium carbonate pentahydrate, or titanium dioxide as an adjuvant. Thus, the experiment clearly shows that when the adjuvants of the invention is included in parenteral vaccine formulations, the amount of antigen necessary to induce an immune response, following one immunisation, is reduced.

Example 2

Immunisations with Vaccine Formulations of the Invention Comprising Either Magnesium Hydroxide, Magnesium Carbonate Pentahydrate, or Titanium Dioxide as an Adjuvant The vaccine formulations were prepared as described above, and the mice were immunised on day 0 and 14 with 1 μg of TT as described above. Blood was drawn every 7 days from day 0 to 42, and serum was prepared and analysed as described above.

Results, given as the geometric mean titre of the whole group, are shown for days 7 and 28 in FIGS. 2A and 2B. The adjuvant used is indicated below each group. As can be seen in FIG. 2A, vaccine formulations comprising either magnesium hydroxide, magnesium carbonate pentahydrate, or titanium dioxide as an adjuvant induce specific immune responses with an earlier onset than vaccine formulations containing Al(OH)$_3$ as an adjuvant. Furthermore, as can be seen in FIG. 2B, following a second vaccination of all mice on day 14, the immune responses induced with vaccine formulations containing either magnesium hydroxide, magnesium carbonate pentahydrate, or titanium dioxide as an adjuvant, induce specific immune responses similar in magnitude to those induced by a vaccine containing Al(OH)$_3$ as an adjuvant.

Thus, when the adjuvant salts are included in parenteral vaccine formulations, a persistent, specific immune response is induced. Furthermore, and earlier onset is observed, and the magnitude of the immune response is comparable to that seen with vaccine formulations containing Al(OH)$_3$ as an adjuvant.

REFERENCES

1. R. K. Gupta, B. E. Rost, E. Relyveld, and G. R. Siber, Adjuvant properties of aluminium and calcium compounds. M. F. Powell and M. J. Newman (Eds.), Vaccine Design. The Subunit and Adjuvant Approach. 1995 Plenum Press, New York, N.Y., pages 229-248
2. J. K. Rao, C. D. Katsetos, M. M. Herman and J. Savory, Experimental aluminium encephalomyelopathy. Relationship to human neurodegenerative disease. Clin. Lab. Med. 18(4), 687-698 viii (December 1998)
3. J. Savory, C. Exley, W. F. Forbes, Y. Huang, J. G. Joshi, T. Kruck. D. R. McLachlan, and I. Wakayama, J. Toxicol. Environ. Health 48(6), 615-635 (30 Aug. 1996)
4. M. J. Newman, Vaccine adjuvants, Exp. Opin. Ther. Patents 10(3), 1-18 (2000)
5. D. T. O'Hagan, G. S. Ott, and G. Van Nest, Recent advances in vaccine adjuvants: the development of MF59 emulsion and polymeric microparticles, Mol. Med. Today 3(2), 69-75 (February 1997)
6. "Vaccine Design. The Subunit and Adjuvant Approach", Chapter 7
7. J. Y. Lee et al.: "Beryllium, an adjuvant that promotes gamma interferon production", Infection and Immunity, Vol. 68, No. 7, 4032-4039 XP002169720 (July 2000)
8. Stas' N. F. et al.: "Modification of Aluminium Hydroxide used as an adjuvant", Database Biosis, Khimiko-Farmatsevticheskii Zhurnal, Vol. 24, No. 7, 65-66 (1990)

The invention claimed is:

1. A parenteral immunogenic composition comprising a liquid solution consisting essentially of (a) at least one immunogenic substance selected from the group consisting of an antigen, an allergen, an allergoid, a peptide, a protein, a hapten, a carbohydrate, a peptide nucleic acid (PNA), a ribonucleic acid (RNA), viral material, bacterial material, a deoxyribonucleic acid (DNA), a parasite, a retrovirus, a toxin, and mycoplasma; and (b) magnesium carbonate hydroxide pentahydrate, wherein magnesium carbonate hydroxide pentahydrate is in suspension.

2. A parenteral immunogenic composition according to claim 1, further comprising an additional adjuvant.

3. A parenteral immunogenic composition according to claim 2, wherein the additional adjuvant is selected from the group consisting of a saponin, MF59, Monophosphoryl lipid A (MPL), polylactide co-glycolide (PLG), polylactide co-glycolide acid (PLGA), calcium phosphate, Freund's incomplete adjuvant (IFA), Freund's complete adjuvant, an interleukin, a glucan, cholera holotoxin, a liposome, muramyl dipeptide, muramyl tripeptide, 1,1,dichloro-2,2,bis(p-chlorophenyl)ethylene (DDE), Dehydroepiandrosterone (DHEA), dimyristoylphosphatidylcholine (DMPC), dimyristoylphosphatidyl-glycerol (DMPG), deoxycholic acid/alum complex (DOC/alum complex), phospatidylethanolamine and an aluminum salt.

4. A parenteral immunogenic composition according to claim 1, further comprising a pharmaceutically acceptable excipient or carrier.

5. A parenteral immunogenic composition according to claim 1, further comprising a diluent, a buffer, a suspending agent, a solubilizing agent, a pH-adjusting agent, a dispersing agent, or a colorant.

6. A parenteral immunogenic composition according to claim 1, for intravenous, intramuscular, intraarticular, subcutaneous, intradermal, epicutaneous, or intraperitoneal administration.

7. A parenteral immunogenic composition according to claim 3, wherein the saponin is selected from the group consisting of Quil A and Qs-21.

8. A method for generating an immune response in an individual, comprising administering to the individual the immunogenic composition of claim 1.

9. The immunogenic composition of claim 1, wherein the immunogen is dissolved in the liquid solution.

10. The parenteral immunogenic composition of claim 1, wherein the immunogenic substance is an allergen or allergoid.

11. A parenteral immunogenic composition comprising (a) at least one immunogenic substance selected from the group consisting of an antigen, an allergen, an allergoid, a peptide, a protein, a hapten, a carbohydrate, a peptide nucleic acid (PNA), a ribonucleic acid (RNA), viral material, bacterial material, a deoxyribonucleic acid (DNA), a parasite, a retrovirus, a toxin, and mycoplasma, and (b) magnesium carbonate hydroxide pentahydrate, and the immunogenic composition is a liquid, wherein magnesium carbonate hydroxide pentahydrate is in suspension.

12. A parenteral immunogenic composition according to claim 11, further comprising an additional adjuvant.

13. A parenteral immunogenic composition according to claim 12, wherein the additional adjuvant is selected from the group consisting of a saponin, MF59, Monophosphoryl lipid A (MPL), polylactide co-glycolide (PLG), polylactide co-glycolide acid (PLGA), calcium phosphate, Freund's incomplete adjuvant (IFA), Freund's complete adjuvant, an interleukin, a glucan, cholera holotoxin, a liposome, muramyl dipeptide, muramyl tripeptide, 1,1,dichloro-2,2,bis(p-chlorophenyl)ethylene (DDE), Dehydroepiandrosterone (DHEA), dimyristoylphosphatidylcholine (DMPC), dimyristoylphosphatidyl-glycerol (DMPG), deoxycholic acid/alum complex (DOC/alum complex), phospatidylethanolamine and an aluminum salt.

14. A parenteral immunogenic composition according to claim 11, further comprising a pharmaceutically acceptable excipient or carrier.

15. A parenteral immunogenic composition according to claim 11, further comprising a diluent, a buffer, a suspending agent, a solubilizing agent, a pH-adjusting agent, a dispersing agent, or a colorant.

16. A parenteral immunogenic composition according to claim 11, for intravenous, intramuscular, intraarticular, subcutaneous, intradermal, epicutaneous, or intraperitoneal administration.

17. A parenteral immunogenic composition according to claim 13, wherein the saponin is selected from the group consisting of Quil A and Qs-21.

18. The immunogenic composition of claim 11, wherein the formulation is suitable for parenteral administration.

19. The immunogenic composition of claim 11, wherein the immunogen is dissolved in the liquid solution.

20. The parenteral immunogenic composition of claim 11, wherein the immunogenic substance is an allergen or allergoid.

* * * * *